United States Patent [19]

Jacobs

[11] Patent Number: 5,895,761
[45] Date of Patent: Apr. 20, 1999

[54] SURFACE AREA LIQUID TRANSFER METHOD AND RELATED APPARATUS

[75] Inventor: Merrit Nyles Jacobs, Fairport, N.Y.

[73] Assignee: Clinical Diagnostic Systems, Inc., Rochester, N.Y.

[21] Appl. No.: 08/094,724

[22] Filed: Jul. 21, 1993

[51] Int. Cl.⁶ .................................................. G01N 35/00
[52] U.S. Cl. ........................... 436/43; 422/63; 422/100
[58] Field of Search ............................. 422/58, 61, 63, 422/99, 100, 62; 436/43–47

[56] References Cited

U.S. PATENT DOCUMENTS

| | | |
|---|---|---|
| 985,574 | 2/1911 | Diskin . |
| 1,750,567 | 3/1930 | Campbell . |
| 2,868,020 | 1/1959 | Williams, Jr. ............................... 73/437 |
| 3,006,317 | 10/1961 | Showalter ................................. 118/212 |
| 3,776,184 | 12/1973 | Harrison .................................. 118/243 |
| 3,842,660 | 10/1974 | Van Buskirk ......................... 73/425.4 P |
| 3,992,158 | 11/1976 | Przybylowicz et al. ..................... 422/56 |
| 4,096,825 | 6/1978 | Golias et al. ............................. 118/221 |
| 4,340,390 | 7/1982 | Collins et al. .............................. 422/63 |
| 4,367,750 | 1/1983 | Levine ...................................... 422/61 |
| 4,615,360 | 10/1986 | Jacobs ....................................... 141/18 |
| 4,826,759 | 5/1989 | Guire et al. ................................ 422/61 |
| 4,906,439 | 3/1990 | Grenner .................................... 422/56 |
| 4,963,325 | 10/1990 | Lennon et al. ............................. 422/61 |
| 4,985,205 | 1/1991 | Fritsche et al. ............................ 422/56 |
| 5,012,758 | 5/1991 | Kunzler ................................... 118/264 |
| 5,143,849 | 9/1992 | Barry et al. ............................... 436/50 |

FOREIGN PATENT DOCUMENTS

| | | | |
|---|---|---|---|
| 0 075 605 A1 | 9/1981 | European Pat. Off. | .......... B01L 3/00 |
| 0 376 110 A2 | 12/1989 | European Pat. Off. | ....... G01N 35/00 |
| 0 459 093 A2 | 3/1991 | European Pat. Off. | ......... C12M 1/32 |
| 3341518 C1 | 4/1985 | Germany | ............................ G01N 1/10 |
| 2 095 404 | 9/1982 | United Kingdom | ............ G01N 1/10 |
| WO 91/01364 | 2/1991 | WIPO | ................................ C12M 1/32 |

Primary Examiner—Lyle A. Alexander
Attorney, Agent, or Firm—Dana M. Schmidt

[57] ABSTRACT

An apparatus and a related method for uniformly transferring a liquid material to a test slide element in which a transfer element having a liquid supporting surface area approximately equal to the surface area subtended by the test volume of the test slide element is brought into direct contact with the test element surface so that the liquid is distributed all at once thereto.

10 Claims, 11 Drawing Sheets

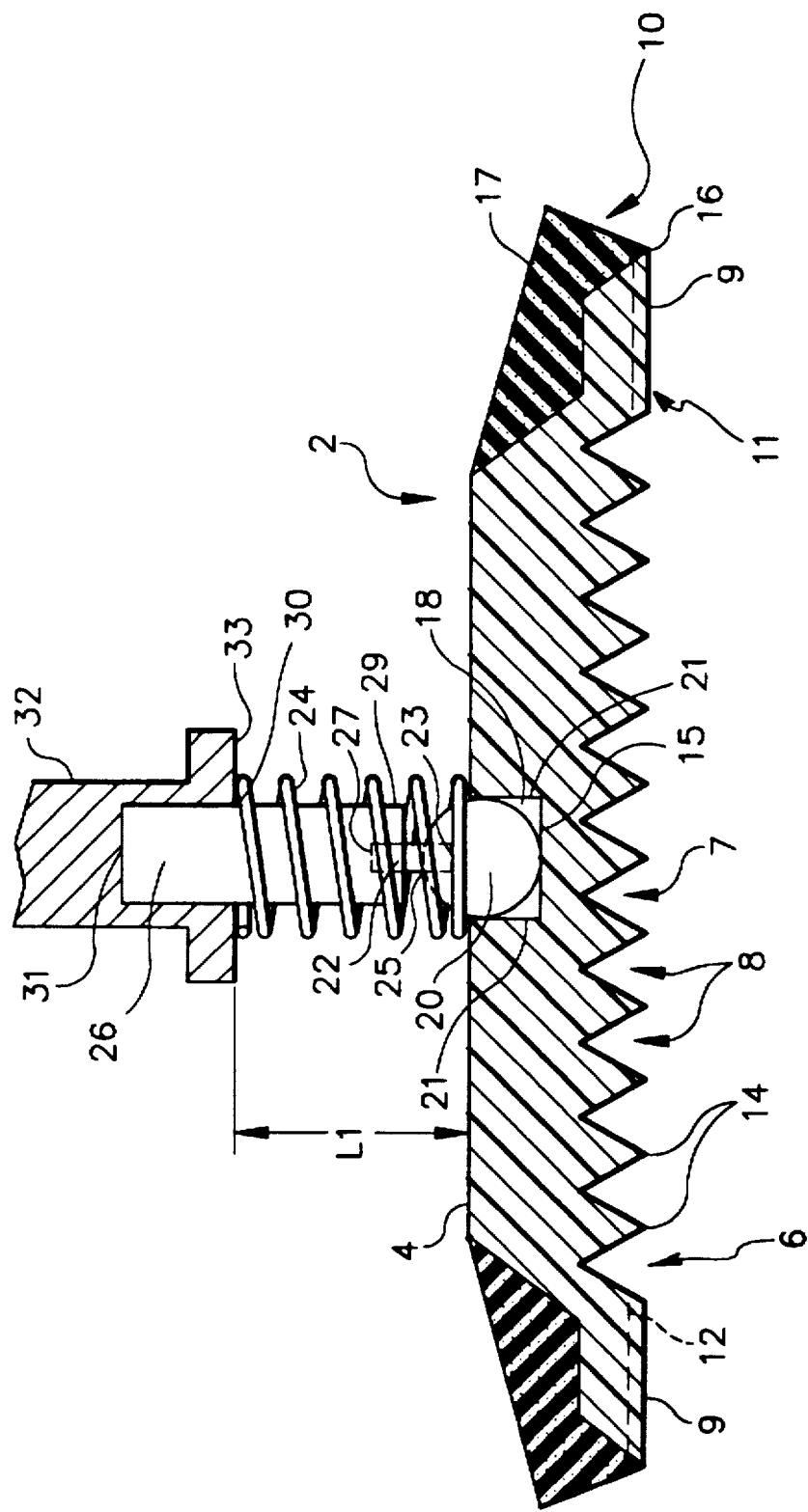

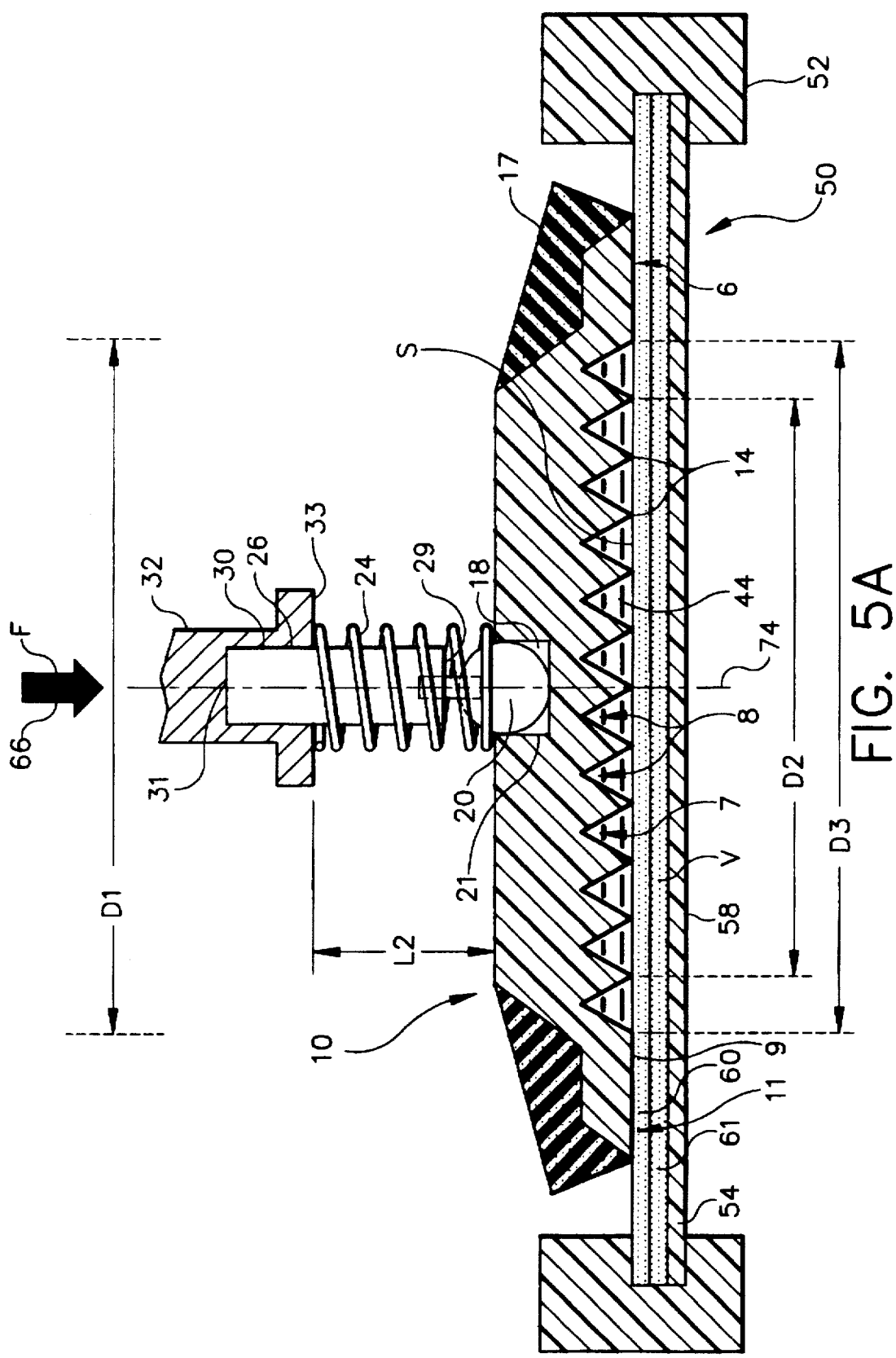

SURFACE AREA LIQUID TRANSFER METHOD AND RELATED APPARATUS

FIELD OF THE INVENTION

The invention is directed to the field of clinical analyzers for the testing of liquid analytes, and in particular to a method and associated apparatus for transferring a patient sample to a test element.

BACKGROUND OF THE INVENTION

In the field of clinical analyzers for the testing of liquid analytes, a patient sample is introduced and caused to interact with a reaction chemistry to produce a signal involving the analyte of choice, for detection by a sensing apparatus. A preferred technique used by analyzers involves the so-called dried assay technology whereby patient sample is applied to dried test slide elements, each having a dried reactant layer. Analyzers and test elements using this technology include those manufactured by Eastman Kodak Company, both under the trademark "EKTACHEM™".

In a conventional operation, a patient sample is conveyed to a processing station within an analyzer at which time a patient sample is dispensed onto the test element. The sample is dispensed by means of a point source, usually a disposable pipette tip, which is positioned a short distance above the test element surface and has a tip orifice from where the sample is expelled (or metered) onto the sample. A metering tip method of dispensing patient liquid is described in U.S. Pat. No. 5,143,849. There are a number of problems relating to a metering technique such as those typically described.

First, it is important to understand that sample delivered from a point source has to spread horizontally, as well as vertically, through the predetermined test volume of the test element. The need for both directions of spreading introduces the possibility of flow irregularities.

Second, the reliability of test results is impacted by the sensitivity occurring due to differences in the makeup of samples between patients. For example, a patient may have a serum, plasma or whole blood sample that may contain a high fat content, (i.e.: containing a higher percentage of lipids and lipo-proteins than a "normal" patient). These sorts of differences are not, however, limited to non-average patients; differences in samples between patients in the so-called "normal" range may also impact the accuracy of test results.

In some cases, the presence of varying amounts of biological components and salts in the patient sample can produce a variation in the sample's viscosity, surface tension and contact angle, impacting its ability to outwardly spread in a uniform manner when dispensed as a drop from a suspended pipette tip onto a test element. Nonuniformity in the spreadability of a patient liquid may affect the accuracy of the detection of the analyte of choice, especially if the analyzer detection means is focused on only a portion of the chemistry portion of the test element onto which a patient sample has been dispensed. This type of nonuniformity is possible with any body fluid, such as blood serum, urine, etc., and may extend as well to control or calibration liquids that are commonly utilized in known clinical analyzers.

The above problems are generally known as "matrix effects" and are based on differences in patient liquid samples, as well as sample interaction with the spreading layer of the chemistry portion of a test element. The spreading layer assists in the migration of the liquid sample across the chemistry portion of the element and in general it works well to counter these effects. An example of a spreading layer is described in greater detail in U.S. Pat. No. 3,992,158.

However, the requirement that a spreading layer be added to the chemistry portion of a test element to promote sample migration is expensive and complex. In addition, and notwithstanding the use of a spreading layer, point source dispensing systems have other drawbacks. For example, it is usually required that an additional volume of patient liquid be dispensed onto the test element to provide a sufficiently uniform detection or read area. Typically as much as 10 microliters of a patient liquid can be required to produce an effective read area having a diameter of 3 mm. This, in turn, also requires that the chemistry portion of the test element be provided with a larger surface area to accept the additional volume of patient liquid dispensed onto the test element. Further, the dispensing of additional quantities of patient liquid from a point source above the test element also increases the probability of outwardly diffusing or washout of the reaction chemistry, effectively diluting the chemical portion of the test element.

There are other effects which may produce test variability that result from dispensing a volume of liquid sample from a point source. The ability of a point source, such as a pipette tip, to adequately target onto a test element so that it can be analyzed is directly influenced by flow characteristics of the liquid to be tested. These characteristics are affected by factors such as the viscosity, surface tension, contact angle and temperature of the liquid, the volume dispensed, shape of the tip nozzle, the distance the tip is suspended above the test element, the centering of the tip above the test slide, and the makeup of the sample to be tested. Other factors such as the amount of ambient air flow in the vicinity of the dispensed liquid, must also be considered, and all factors may impact upon the accuracy of results. In addition, it is also known that liquid dispensed by a suspended point source has a tendency to move up the exterior surface of the dispensing container, rather than down onto the test element designed to receive the liquid. This problem, known as perfusion, has been an occasional but persistent problem with clinical analyzers using the dispensing means described, altering the volume of liquid that is subsequently dispensed. In addition, the horizontal or outward flow of a point source dispensed liquid varies over time, affecting in particular rate-type chemistries which are also time dependent.

There is, therefore, a need to provide a metering method which will allow patient liquid to be deposited onto a test element without the variability in testing results which are possible using known point source techniques.

There is also a need to provide a method of dispensing a smaller quantity of a patient liquid onto a test element in a substantially uniform manner which will minimize the flow characteristics of the dispensed liquid, as well as washout, and produce an effective detection area for an analyzer.

There is a further need to provide a method of dispensing a patient sample to a test element which will obviate the current needs of requiring a spreading layer to horizontally and uniformly spread a liquid patient sample over the detection area of a test element, thereby also simplifying their design and manufacture.

RELATED APPLICATIONS

Reference is made to copending and commonly assigned application Ser. Nos. 08/094,722 and 08/094,668 filed concurrently herewith by Merrit N. Jacobs and entitled: "Method of Pretreating of Test Slide Elements", Docket 65709.2 and "Whole Blood Metering Cup", Docket 65710.

SUMMARY OF THE INVENTION

The present invention solves the above stated needs by providing a method and related means of metering a sample onto a test element without concern for the effects of fluid adhesion or flow characteristics of a particular biological liquid that occur when dispensing from conventional point source metering systems onto a relatively large test slide surface area.

More specifically, in accord with one aspect of the invention, there is provided a method of dispensing a liquid sample onto a test element, the test element having a test volume subtending a surface area for that volume for receiving the sample, the method comprising the steps of:

a) applying onto a transfer element having a liquid-supporting surface for supporting a liquid, a quantity of liquid sample over all of the liquid-supporting surface, and, b) placing the transfer element supporting surface in contact with the entirety of the test surface area of a test element all at once, thereby transferring the liquid sample as a surface-dispersed quantity to the test element without the need for horizontal flow over the test surface area.

In accord with another aspect of the invention there is provided a liquid dispensing device, useful for analyzers for the testing of liquid analytes, the device comprising a main body, a transfer element supported by the main body for engagement with a test element having a liquid-impermeable surface for supporting a liquid over an area approximately equal to the area of the test surface of the test element, and means disposed about the periphery of the transfer element for absorbing excess liquid from the supporting surface prior to dispensing therefrom.

Thus, it is an advantageous feature of the invention that a method and associated apparatus are provided in which a liquid sample can be applied onto a test slide element which prespreads the liquid uniformly over a contact surface area that matches the test element test-surface area, thus negating the matrix effects which impact the diffusivity of conventionally dispensed systems.

Another advantageous feature of the invention is that a smaller quantity of liquid can be directly and evenly applied to the test volume of a test element with reduced consideration of the fluid characteristics of a dispensed liquid from a suspended tip.

A further advantageous feature of the invention is that the ability to uniformly dispense a patient liquid onto a test element eliminates the necessity for a test element having a preincorporated horizontally diffusing spreading layer thereby allowing test elements to be manufactured more easily and inexpensively.

A still further advantageous feature of the present invention is that by uniformly distributing a patient sample to the test volume of a test element there is provide less need for an oversized chemistry portion to provide an adequately sized detection area, thereby producing an additional and significant savings in the manufacture of test elements.

A still further advantageous feature of the present invention is that a surface-dispersed quantity, as defined below, can be delivered to the test volume of a test element all at once, providing a relatively constant concentration level of liquid across the detection read area without significant washout of the dried chemistry or transient liquid flow after delivery.

Other advantageous features will become apparent upon reference to the following Description of the Preferred Embodiments, when read in light of the attached drawings.

DESCRIPTION OF THE DRAWINGS

FIG. 1 is a fragmentary side elevational view, in section, of a fluid dispensing apparatus according to the present invention.

FIGS. 5(a) and 5(b) are fragmentary side elevational views, in section, of the apparatus shown in FIGS. 1-4 illustrating the instantaneous dispensing of a patient liquid onto the entire test surface of a test element.

DETAILED DESCRIPTION OF THE PREFERRED EMBODIMENTS

The invention is hereinafter described in the context of the preferred embodiments. In addition, the invention is useful regardless of the liquid being dispensed, the kind of analyzer that is being used, and regardless of whether the surface is a dried slide test element, or even any kind of test element, since the described methods and associated apparatus can also be used to meter onto any surface.

Terms such as "up", "down", "lower", "vertical", "horizontal", and "bottom" as used herein refer to the orientation of parts when the apparatus is positioned in its customary position of use. The term "surface-dispersed quantity" means, a quantity in which the surface area/volume ratio is approximately 1:1, e.g., if a 10 cc volume has a 10 $cm^2$ dispersed surface area and a 1 cm thickness, its ratio is 1:1. Ratios of 9:10 or 11:10 are included here.

Figure 2A:
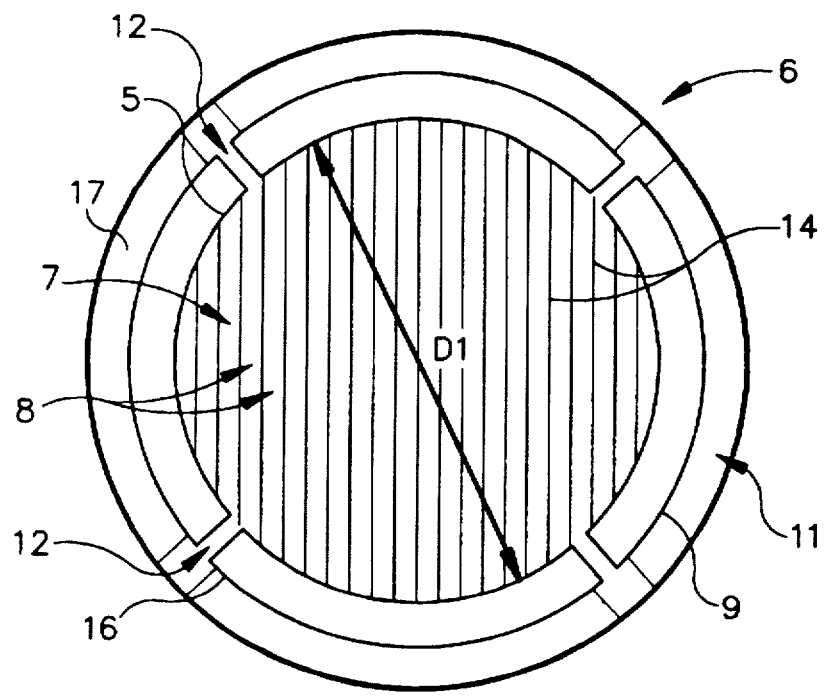
FIGS. 2(a) and 2(b) are bottom views of the apparatus shown in FIG. 1 illustrating preferred embodiments of a lower liquid-supporting surface of the apparatus.
Figure 2B:
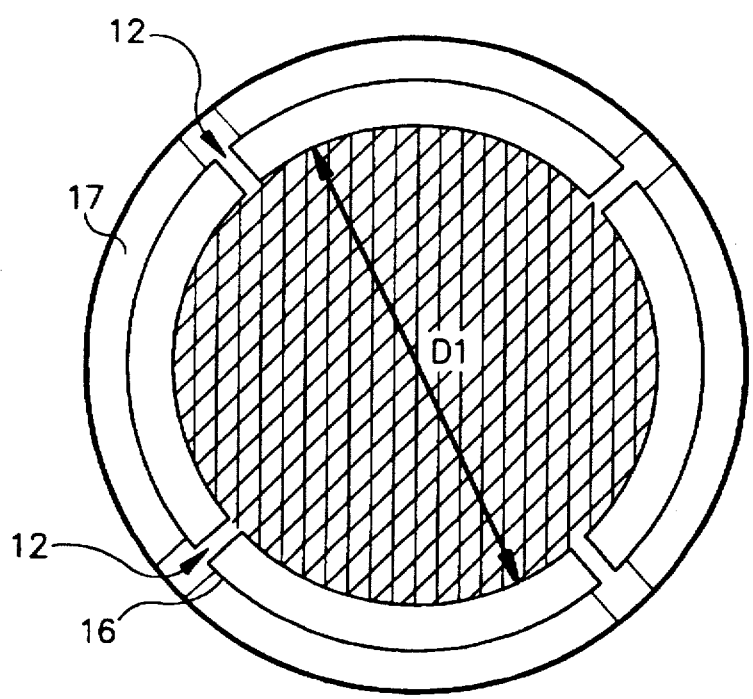

A preferred embodiment of the present invention is shown in FIGS. 1, 2(a), and 2(b).

Referring to FIG. 1, a transfer element 10 is shown having a main body 2 comprising an upper surface 4 and a preferably circular lower surface 6. The shape of lower surface 6 may be varied, but preferably should be congruent with the shape of the test surface area to be contacted, whatever that may be.

Referring to FIG. 2(a), lower surface 6 is defined, in part, by a liquid-supporting portion 7 defined by a series of substantially parallel, V-shaped grooves 8, disposed over the majority of the area of surface 6. The shapes and depths of grooves 8, however, may be varied to be rectangular, convex, concave, U-shaped, etc. Alternate configurations can also be provided for defining liquid supporting portion 7; for example, a diamond-like pattern such as illustrated in FIG. 2(b). In the embodiment illustrated in FIGS. 1 and 2(a), grooves 8 have a depth of about 200 microns and a spacing of about 400 microns.

Further, liquid-supporting portion 7 can alternatively be textured (not shown), as opposed to providing grooves, provided capability is provided for supporting a sufficient quantity of liquid to effectively coat the reagent member, or other reactive portion of a test element.

Lower surface 6 is further defined by a ring portion 11, preferably circumferentially and substantially disposed about the entire outer periphery 5 of liquid-supporting portion 7, and having an outer peripheral edge 16. Preferably, ring and liquid-supporting portions 7, 11 are made from the same material, except that ring portion 11 is smooth. Though main body 2, FIG. 1, can be constructed of almost any material, it is preferred that lower surface 6 be made from a compliant and liquid-impermeable material. In the embodiment illustrated, main body 2, including lower surface 6, is made from a plastic with minimal protein adhesion, such as polypropylene or polyethylene. Ring portion 11 and liquid-supporting portion 7 further define a diameter D1 which is preferably at least equal to the detection or read area of the chemistry portion of a test element.

Referring to FIGS. 1 and 2(a), grooves 8 are formed in surface 6 between ring portion 11, to form a series of ribs 14. In the present embodiment, ribs 14 are rounded, though this may not be required if lower surface 6 is made from a fairly compliant material, so as not to damage the chemistry portion of a test element when brought into contact therewith. Contacting surface 9 of ring portion 11 is made to be flush with ribs 14, ring portion 11 being substantially continuous with the exception of a variable number of small vent channels 12.

To absorb excess liquid at the periphery of surface 6, a disc 17, FIG. 1, made of a liquid absorbant material is preferably continuously disposed about main body 2, adjacent outer peripheral edge 16 and generally in contact with ring portion 11, except in the vicinity of vent channels 12, FIG. 2, where it is slightly undercut so as not to prematurely siphon liquid from grooves 8. Alternately, cross-channels (not shown) arranged substantially perpendicular to grooves 8 can also be provided across surface 6 for this purpose. In the embodiment illustrated, disc 17 is made of a high density open-cell urethane foam, though other nonreactive, liquid absorbing materials such as an absorbant paper may be provided. Disc 17 is made to extend inwardly radially from edge 16, attaching to upper surface 4.

Transfer element 10 is preferably made to be both pivotably and vertically movable. Referring to FIG. 1, a ball 20, is seated within a centrally disposed recess 18 defined in upper surface 4. Preferably, recess 18 is an opening sized to receive ball 20 and is defined by a substantially orthogonal configuration, having a bottom surface 15 and side seating surfaces 21. Ball 20, in the embodiment illustrated, is made of Delrin™, a polyformaldehyde acetal resin sold by E. I. DuPont de Nemours & Company, though other moldable plastics such as polyethylene or polycarbonate are also acceptable. It is preferable, however, that ball 20 be provided with a relatively smooth outer surface for allowing ball 20 to be engagably movable within recess 18 and along side seating surfaces 21.

One end 23 of a mounting arm 22 is threaded or otherwise fastened into a bore 25 defined in ball 20, bore 25 being oppositely situated from the portion of ball 20 which is engaged into recess 18. The remaining end 27 of mounting arm 22 extends upwardly, in the embodiment illustrated, and is engaged into lower end 29 of a cylindrical supporting member 26. The other or upper end 31 of supporting member 26 is inserted into a force-application member 32, having a centrally disposed sleeve 30. In the embodiment illustrated, supporting member 26 is shaped so as to be slidingly engageable within sleeve 30. To bias element 10 to be generally perpendicular to axis 74, FIG. 5A, a helical spring 24, having a length L1, is positioned between upper surface 4 and a lower surface 33 of force application member 32, and is circumferentially disposed about supporting member 26. Force application member 32 is mechanically attached to an analyzer (not shown). In the embodiment illustrated, ball 20, mounting arm 22, spring 24, supporting member 26, and force application member 32 can be made part of transfer element 10, or be part of the analyzer, the remainder of which is not shown. It can be seen that other available means of making the transfer element pivotable can be used, such as by providing supporting member 26 from a flexible material so as to allow it to bend from a neutral position.

FIGS. 3(a) through 6 illustrate a method of dispensing a quantity of liquid sample, such as blood serum, onto a test element that permits the quantitative analysis of analytes in the liquid sample using the apparatus discussed above and illustrated in FIGS. 1 and 2.

Figure 3A:
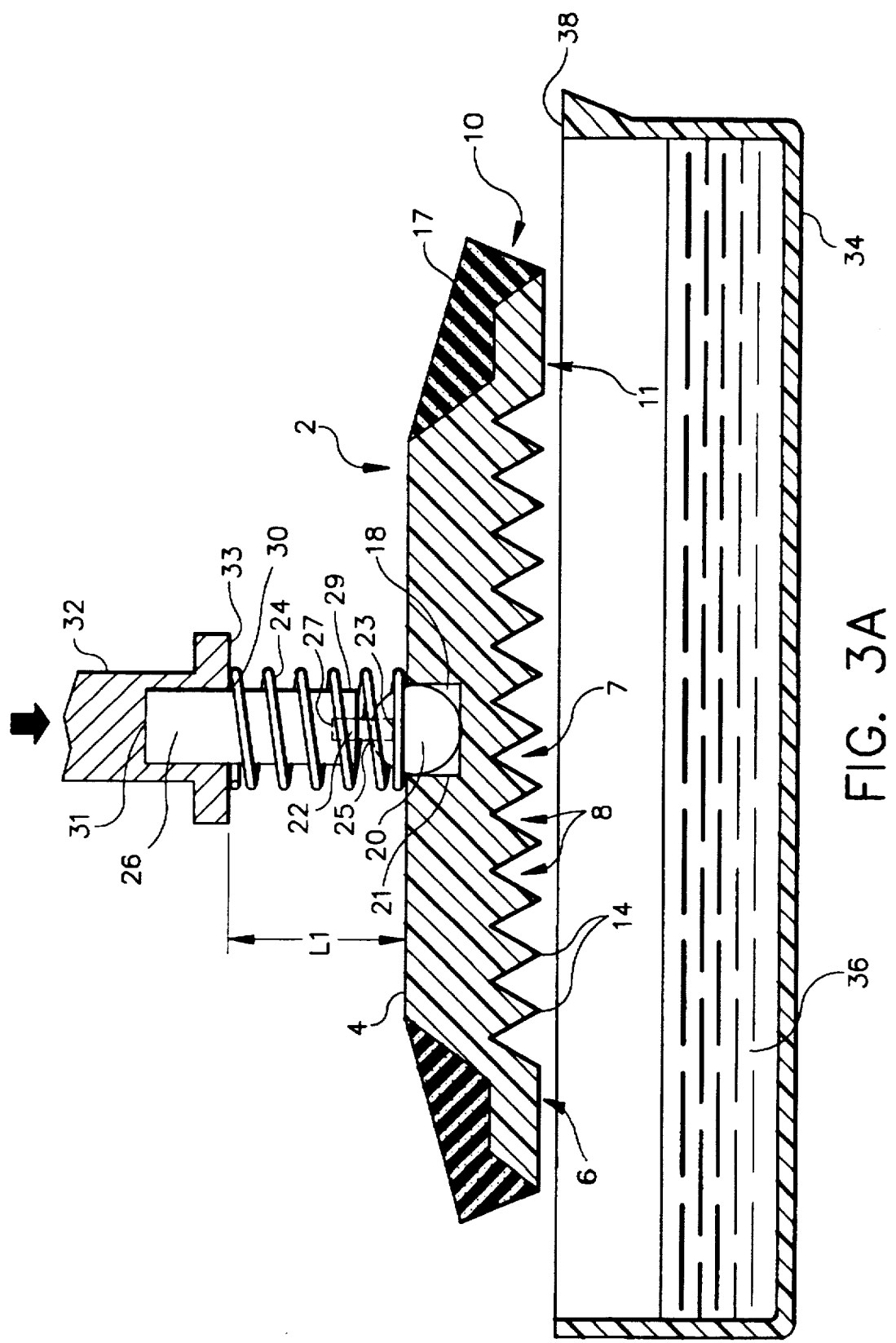
FIGS. 3(a) and 3(b) are fragmentary side elevational views, in section, of the apparatus shown in FIG. 1, illustrating the transfer of a liquid from a source to the liquid-supporting surface of the apparatus of FIGS. 1 and 2(a).
Figure 3B:
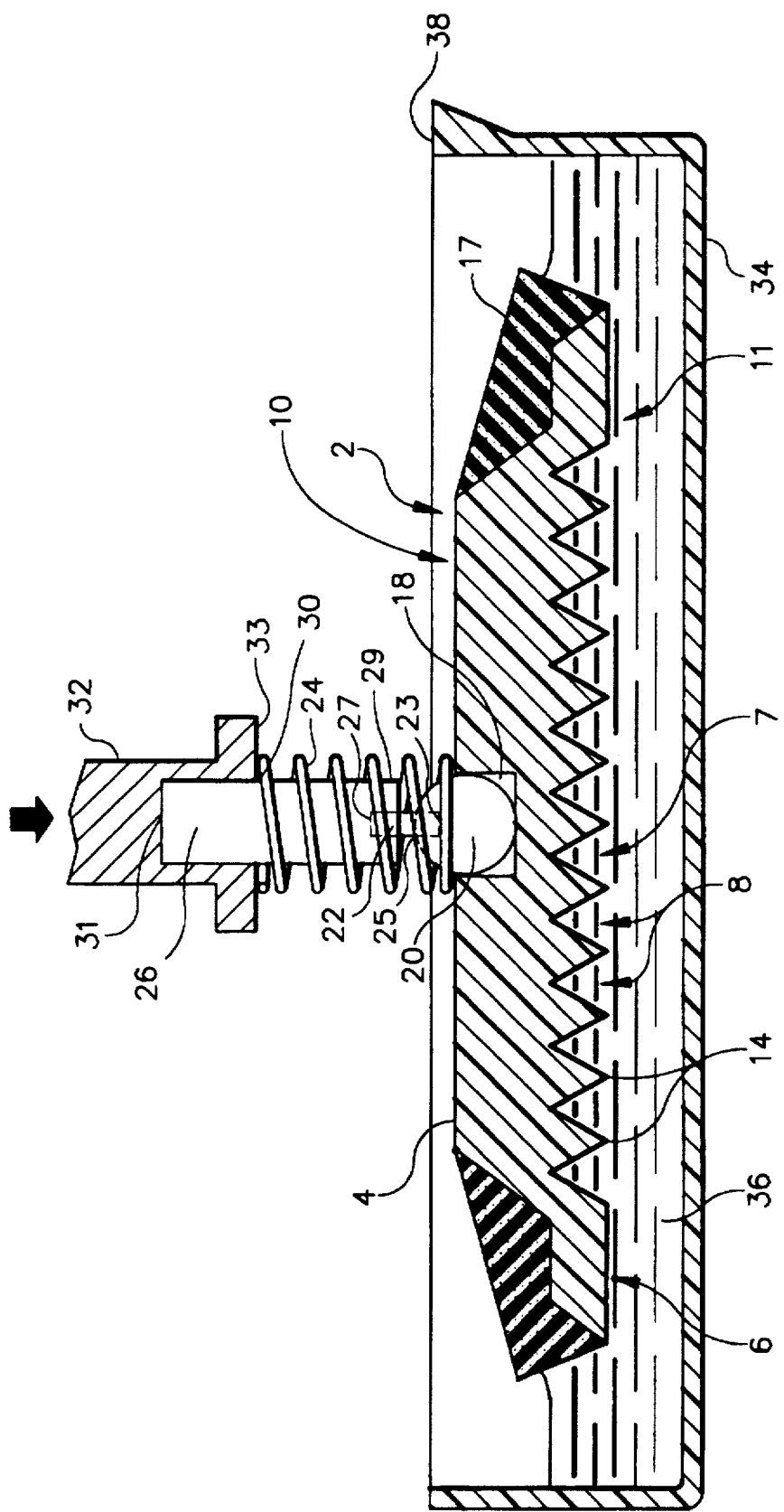

Turning to FIGS. 3(a) and 3(b), transfer element 10 is placed into a container 34 containing a patient liquid 36. The location and requirements of container 34 can be varied such that it may be positioned at a station within the confines of a clinical analyzer, or alternatively in an offline position. Container 34, in terms of location or configuration, is not considered an essential element of the present invention.

Figure 4A:
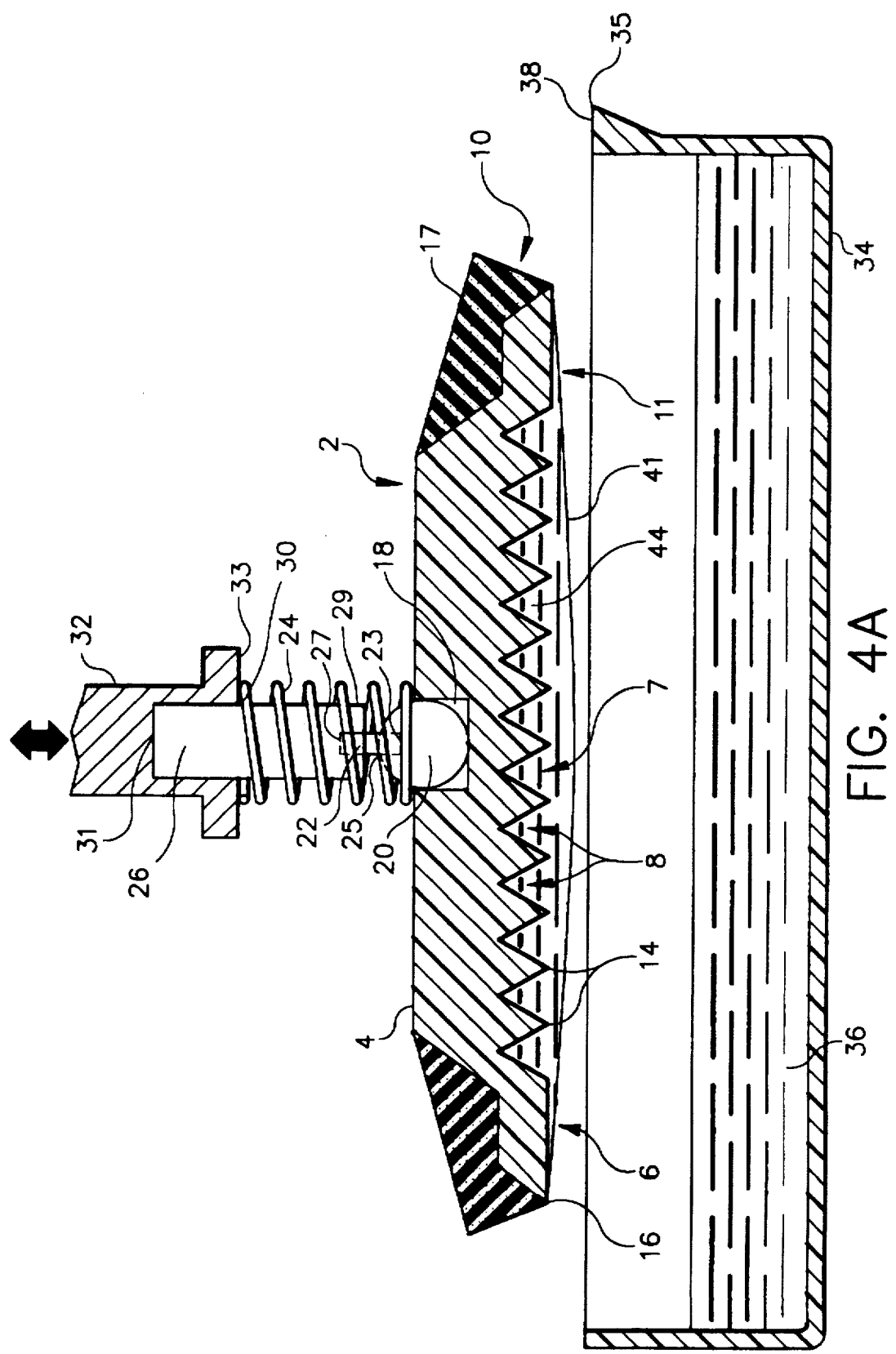
FIGS. 4(a) and 4(b) are fragmentary side elevational views, partially in section, of the apparatus shown in FIGS. 1-3, illustrating the removal of excess fluid from the liquid-supporting surface prior to the dispensing of fluid onto a test element.

Transfer element 10 is first lowered into container 34, as illustrated in FIG. 3(b), immersing lower surface 6 to a level in which grooves 8 of liquid-supporting portion 7, if present, can acquire contained patient liquid 36 thereupon. Most of the air contained within grooves 8 is vented outwardly of transfer element 10 through venting channels 12, FIG. 2(a). Transfer element 10 is then withdrawn from container 34. As shown in FIG. 4(a), as transfer element 10 is removed from container 34 a quantity of liquid 44 is retained on supporting portion 7, such as within grooves 8 due to the adhesion of fluid to ribs 14.

Figure 4B:
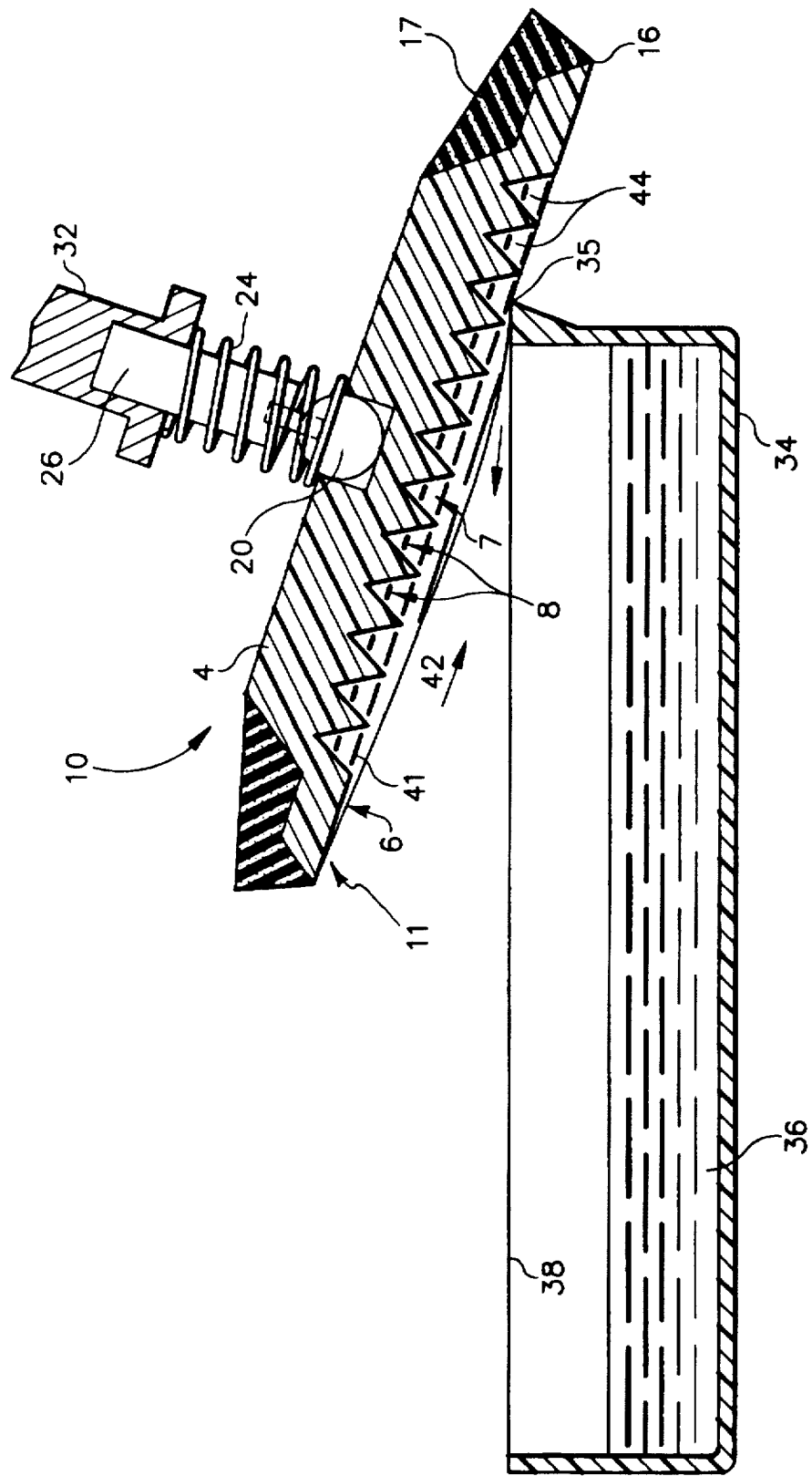

As transfer element 10 is withdrawn from container 34 a meniscus 41, containing an excess of patient liquid in addition to quantity 44, FIG. 4(b) required to fill grooves 8, forms on lower surface 6 due to the surface tension of the patient liquid. It is preferable that meniscus 41 be removed prior to the dispensing of liquid from transfer element 10 in order to avoid potential flooding of the test slide element when liquid is transferred, and further to more adequately control the volume of liquid to be applied thereto.

Container 34, preferably, provides means for scraping against lower surface 6 to wipe excess liquid from surface 6 and grooves 8. Specifically, an edge 38 is provided with a knife edge 35 as shown in FIG. 4(a) and 4(b). Beginning at one side of liquid-supporting portion 7, transfer element 10 can be drawn, arrow 42, along knife edge 35, to remove meniscus 41, FIG. 4(b), leaving a uniform layer of patient liquid 44 within grooves 8. As lower surface 6 is drawn across knife edge 35 the excess fluid comprising meniscus 41 is squeegeed from one side of lower surface 6 to the other while a quantity of fluid 44 within grooves 8 remains. In addition, the external energy supplied to grooves 8 by scraping knife edge 35 against surface 6 serves to evacuate air pockets formed within grooves 8, allowing the grooves to fill with liquid.

Any small portion of meniscus 41 remaining along the outer peripheral edge 16 of ring portion 11 after lower surface 6 has been drawn along knife edge 35 can then be wicked by the circumferentially disposed absorbent disc 17, positioned adjacent outer edge 16.

Knife edge 35 can be made from known materials. Alternatively, scraping apparatus 38 can be made part of the analyzer, such as if container 34 is located offline.

In this way, a known volume of liquid material 44, as defined by the size and number of grooves 8, is uniformly supported by surface 6 prior to transferring liquid material to a test element. In the embodiment illustrated, a quantity of about 2 microliters is retained within grooves 8, over a diameter D1 of about 4 mm.

Figure 5B:
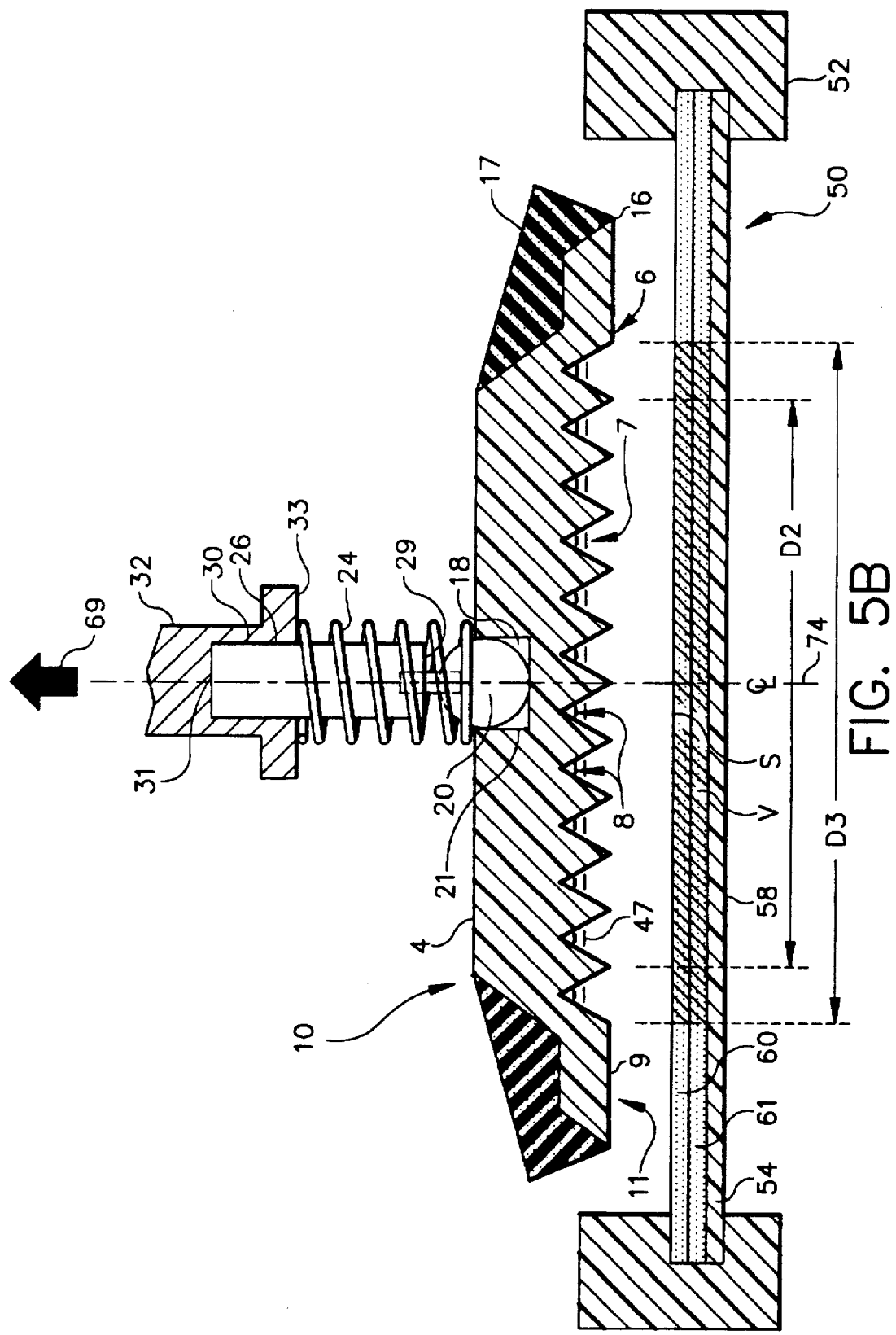

Turning to FIGS. 5(a) and 5(b), transfer element 10 is positioned over a test element 50 having a plastic support frame 52, and a centrally disposed chemistry portion 58 having a circular configuration, a test volume V subtending test surface area S, and having a diameter D3. The chemistry portion 58 further comprises dried reagents distributed through two layers 60, 61 on a support 54. In the embodiment illustrated, D3 is also about 4 mm.

Figure 7:
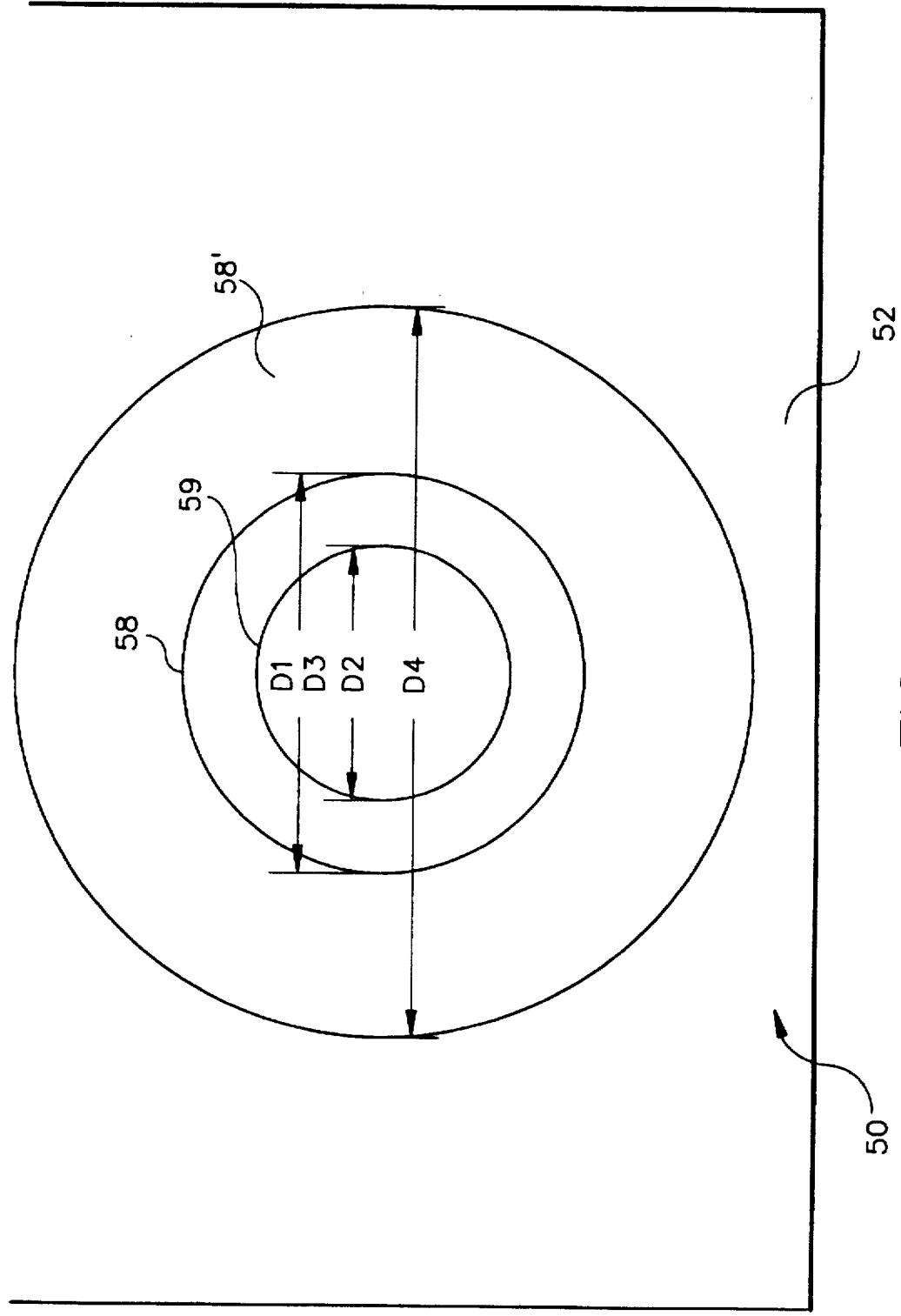
FIG. 7 is a partial top view of the test element shown in FIGS. 5(a) and 5(b) after a liquid has been dispensed thereto illustrating the sizing of a chemistry portion of the test element in accordance with the present invention with that of a known test element.

Referring to FIGS. 5(a), 5(b) and 7, transfer element 10 is lowered until ribs 14 are brought into contact with chemistry portion 58, and specifically, reagent layer 60. As noted above, liquid-supporting portion 7 of lower surface 6 has a diameter D1 which is preferably at least equal to diameter D2, FIG. 5(b), FIG. 7, of detection target area 59 of chemistry portion 58. In the embodiment illustrated, chemistry portion 58 has a diameter D1 of about 4 mm and detection target area diameter D2 is equal to about 3 mm. Such equality of diameters removes the need to have horizontal spreading of the liquid across test volume V.

Referring to FIG. 5(a), downward pressure in the amount of force F is then exerted by force applicating member 32, as shown by arrows 66 substantially along a vertically extending centerline 74. As force F is applied supporting member 26 is further engaged into sleeve 30 and the distance between surface 33 and upper surface 4 is decreased to L2, placing helical spring 24 into compressive contact with upper surface 4, centrally distributing the applied compressive force F to transfer element 10. The effect of providing compressive force F is that liquid-supporting portion 7 and chemistry portion 58 are also brought into compressive contact.

Under force F, liquid 44 contained within each of grooves 8 is then uniformly communicated to the entirety of test surface area S of test volume V, effectively blotting the entire test surface area S all at once as a surface-dispersed quantity, as defined, upon removal of transfer element 10, FIG. 5(b). Liquid 44 is then quickly absorbed (or vertically diffused) by porous reactant layers 60, 61. The representation in FIG. 5(b) illustrates the instantaneous dispensing of liquid prior to the complete vertical absorption into porous layers 60, 61. In addition, disc 17 is effective in absorbing excess liquid from outer peripheral edge 16 when each of the surfaces are brought into compressive contact, so as not to flood test element 50. Ring portion 11, having a surface 9 which is flush with edges 14, however, provides a barrier so that only excess liquid is wicked by disc 17 upon contact.

Figure 6:
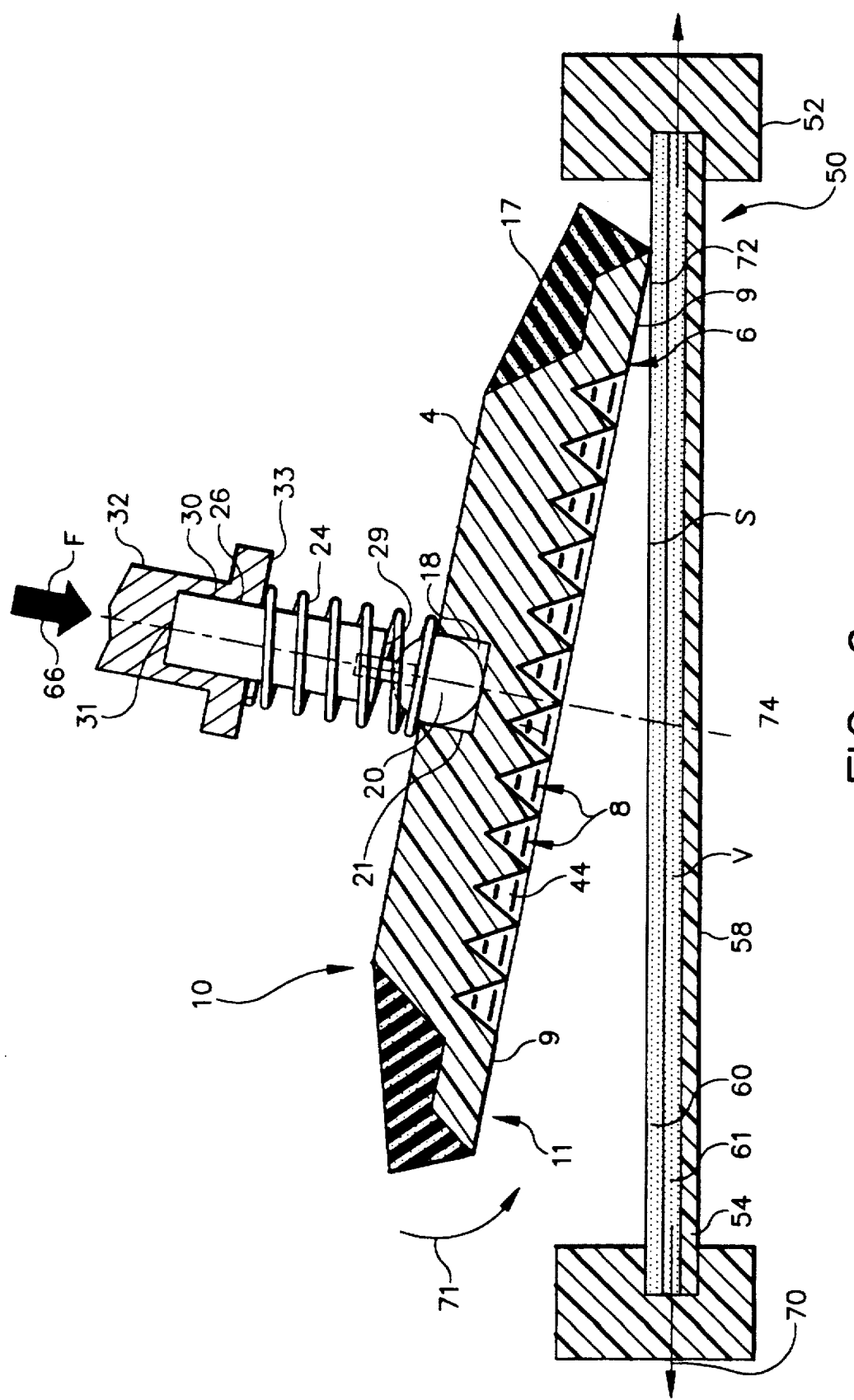
FIG. 6 is a fragmentary side elevational view, shown partially in section, of the fluid dispensing apparatus shown in FIGS. 1-5 illustrating the dispensing of liquid onto a misaligned test element.

FIG. 6 illustrates an optional pivotability feature of transfer element 10 in the event that slide element 50 is not aligned with respect to lower surface 6. According to FIG. 6, the position of slide element 50 defines a plane 70, plane 70 being skewed from vertical centerline 74 such that plane 70 is not orthogonal thereto. As liquid-supporting portion 7 contacts chemistry portion 58 of slide element 50 at one end 72, transfer element 10 is made to pivot about centerline 74 due to downward force F, thereby allowing surface 6 to align substantially parallel to plane 70 as ball 20 impinges upon side surfaces 21 of recess 18 allowing transfer element 10 to rotate counterclockwise, as illustrated by arrow 71, until surface 6 contacts end 75.

The compressive load levels applied also insures chemistry portion 58 will not be damaged. In the embodiment illustrated, a compressive force of about 0.5 ounces is sufficient to transfer a patient liquid to chemistry portion 58 without damage thereto. The amount of force required, however, can be varied depending upon material properties and the fragility of the chemistry portion provided. In addition, rounding the ribs 14 of liquid-supporting portion 7 is also preferable to avoid damage to chemistry portion 58. Transfer element 10 is then withdrawn from slide test element 50 as illustrated in FIG. 5(b), by arrow 69.

The method herein described eliminates the need for a spreading layer to horizontally diffuse the patient fluid throughout reagent layers 60, 61 in that the liquid sample has been effectively and uniformly distributed over the entire surface area, all at once, as a surface-dispersed quantity to the test volume V of element 50, to permit detection of the analyte of interest. Thereby the manufacture of test slide elements, and in particular the manufacture of the chemistry portion contained therein, is simplified.

Figure 8A:
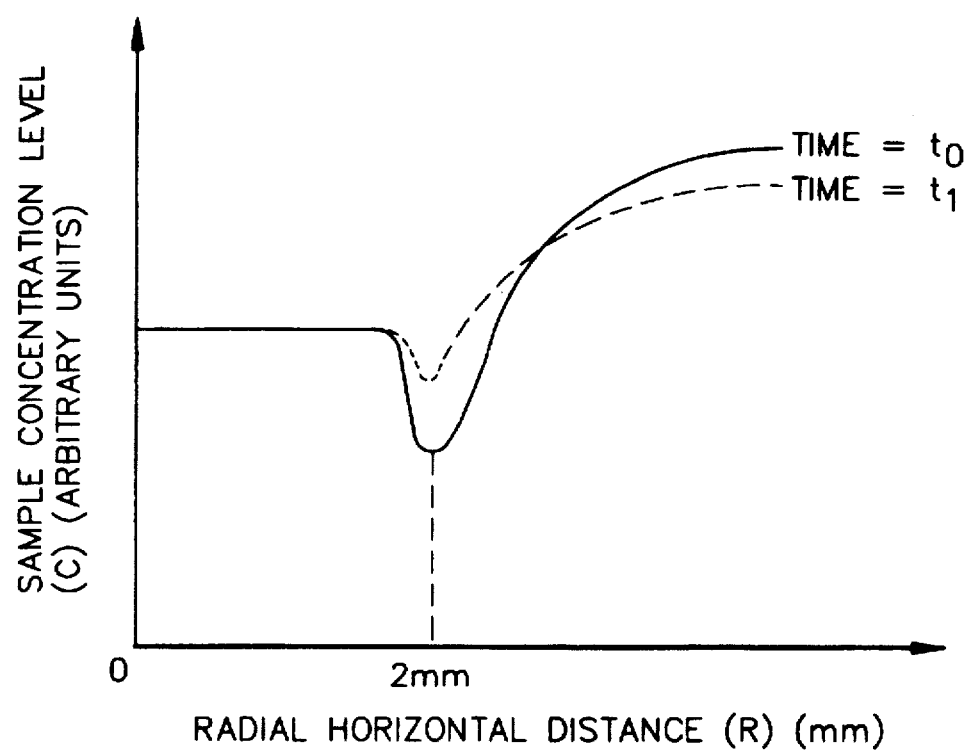
FIGS. 8(a) and 8(b) are plots illustrating the advantageous features of liquid delivered to a test element using the invention shown by FIGS. 1-7 as compared with prior delivery systems.
Figure 8B:
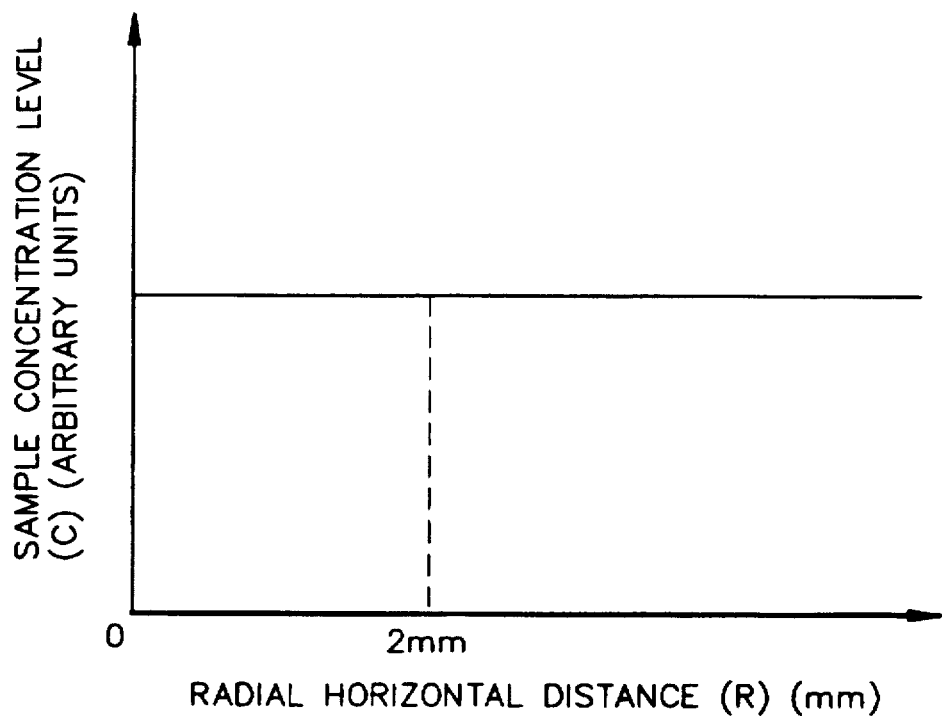

A direct advantage realized by delivering the liquid sample as a surface-dispersed quantity is graphically illustrated in FIGS. 8(a) and 8(b). FIG. 8(a) depicts a generalized plot of sample concentration (denoted as C) versus horizontal radial distance from centerline 74, FIG. 5(a) for a point source dispensing system as typically described above. As noted by the plot, at time to the concentration level C begins to become variable markedly at approximately 2 mm, which is approximately the dimension of the pipette tip exterior diameter as the tip vertically delivers the sample as a single droplet to the test element. A variable level of C is thereafter found as R increases outwardly due to the outward spread of the variably viscous sample liquid from the centrally disposed droplet.

At some later time, $t_1$, there is a tendency for the concentration gradient to equilibrate, or redistribute, to some degree due to diffusion, as represented by the dashed profile. In the embodiment illustrated, $t_1$ is about 1 to 5 minutes, though the time taken to equilibrate, or redistribute can be varied depending upon the diffusivity of compounds used. Such a transient change in the concentration level can directly affect the detection results as read by an analyzer, particularly in rate-type chemistries. Further, the time required for complete equilibration is lengthy and generally unpredictable due to the makeup of individual samples.

By delivering a surface-dispersed quantity all at once to test volume V, FIG. 5(a), a relatively constant concentration level C is provided over the entirety of test surface area S, FIG. 5(a), shown generally by FIG. 8(b). Further, there is no need for the liquid level delivered to equilibrate and no significant and artificial rate change is produced, such as shown in FIG. 8(a).

Referring to FIG. 7, a further advantage provided by the present invention is shown. The chemistry portion 58', of a typical test element 50, having a sample dispensed from a point source (not shown), has a diameter D4 of at least about 11 mm to provide a detection or read area 59 having a diameter D2 of about 3 mm. The present invention, however, by delivering a quantity of patient liquid all at once to an area at least equal to detection area 59 requires a smaller chemistry portion 58. In the embodiment illustrated, chemistry portion 58 has a diameter D3 of about 4 mm, or roughly the same size D1 of lower surface 6. As noted above, because a much small chemistry portion is required, a correspondingly smaller quantity of sample is required to fill the volume. In the embodiment described, approximately 2 microliters is required to fill the smaller chemistry portion 58, as opposed to 10 microliters or more being required for point source dispensing systems having larger chemistry portions.

In another embodiment, a quantity of a liquid diluent can be directly applied all at once to the chemistry portion of a test element using the method and apparatus described herein, prior to the application of a patient sample. This particular embodiment is described in detail in copending and commonly assigned application filed concurrently herewith by Merrit N. Jacobs and entitled: "Method of Pretreating Diagnostic Test Elements", hereby incorporated by reference.

The invention has been described in detail with particular reference to preferred embodiments thereof, but it will be understood that variations and modifications can be effected within the scope of the invention.

What is claimed is:

1. A method of dispensing a liquid sample onto a test element, said element having a test volume subtending a surface area for that volume for receiving said sample, the method comprising the steps of:
   a) applying onto a transfer element having a liquid-impermeable surface for supporting a liquid, a quantity of liquid sample over substantially all of said supporting surface, and
   b) placing the transfer element liquid-supporting surface in contact with all of said surface area of a test element at once, thereby transferring substantially all of the liquid sample on said surface of said transfer element as a surface-dispersed quantity to said test element without the need for extensive horizontal flow over said test element surface area.

2. A method as claimed in claim 1 further comprising the step of removing excess liquid material from said transfer element surface prior to said placing step.

3. A liquid dispensing device useful for analyzers for the testing of liquid analytes, said device comprising:
   a main body,
   a transfer element supported by said main body for engagement with a test element, said transfer element having a liquid-impermeable surface for supporting a liquid over an area approximately equal to the area of the test surface of a said test element, and
   means disposed about the periphery of said contact element for absorbing excess liquid from said supporting surface prior to dispensing therefrom.

4. A device as claimed in claim 3 wherein said absorbing means comprises at least one strip of absorbing material, said strip being disposed about at least a portion of the periphery of said transfer element and in contact with at least a portion of said supporting surface.

5. A device as claimed in claim 3 further comprising means for pivotably adjusting said transfer element to compensate for misalignment with a test element surface, insuring substantial contact with said test element surface for dispensing thereto.

6. A device as claimed in claim 5 further comprising means for biasing said transfer element to be generally perpendicular to a central axis, said biasing means cooperating with said pivotable adjusting means to hold said supporting surface in contact with said slide element surface.

7. A device as claimed in claim 3 wherein said transfer element supporting surface comprises a plurality of grooves, said grooves being sized to support a quantity of liquid for dispensing.

8. A device as claimed in claim 7 wherein said grooves are arranged in a diamond shape pattern extending substantially over the entirety of said supporting surface.

9. A device as claimed in claim 3 further comprising means for wiping excess liquid material from said supporting surface prior to contacting a said test element.

10. A device as claimed in claim 9 wherein said wiping means comprises a knife edge fixture, said fixture being sized so said contacting surface can be scraped against said knife edge to remove excess liquid material prior to contacting with a test element for dispensing liquid thereto.

* * * * *